(12) United States Patent
Choi et al.

(10) Patent No.: US 9,939,378 B2
(45) Date of Patent: Apr. 10, 2018

(54) REAL TIME OPTICAL DETECTION OF BACTERIA

(71) Applicant: Veritide Limited, Addington (NZ)

(72) Inventors: Joon Koo Choi, Christchurch (NZ); Robert Ian Johnston, Christchurch (NZ)

(73) Assignee: Veritide Limited, Addington (NZ)

( * ) Notice: Subject to any disclaimer, the term of this patent is extended or adjusted under 35 U.S.C. 154(b) by 290 days.

(21) Appl. No.: 14/404,788

(22) PCT Filed: Jun. 4, 2013

(86) PCT No.: PCT/NZ2013/000094
§ 371 (c)(1),
(2) Date: Dec. 1, 2014

(87) PCT Pub. No.: WO2013/180583
PCT Pub. Date: Dec. 5, 2013

(65) Prior Publication Data
US 2015/0330898 A1   Nov. 19, 2015

(30) Foreign Application Priority Data

Jun. 1, 2012 (NZ) ........................ 600404

(51) Int. Cl.
*G01N 33/48* (2006.01)
*G01N 21/64* (2006.01)
(Continued)

(52) U.S. Cl.
CPC .............. *G01N 21/64* (2013.01); *C12Q 1/04* (2013.01); *G01J 3/0218* (2013.01); *G01J 3/36* (2013.01);
(Continued)

(58) Field of Classification Search
None
See application file for complete search history.

(56) References Cited

U.S. PATENT DOCUMENTS 5,701,012 A * 12/1997 Ho ..................... G01N 15/1459
250/461.2
7,132,254 B2 * 11/2006 Vincent .................. G01N 21/31
356/213
(Continued)

FOREIGN PATENT DOCUMENTS

| CN | 1823269 | 8/2006 |
|---|---|---|
| CN | 101712926 | 5/2010 |
| CN | 102103081 | 6/2011 |

OTHER PUBLICATIONS

Sagi et al., Sensors and Actuators B 90 (2003) 2-8.*
(Continued)

*Primary Examiner* — Larry D Riggs, II
(74) *Attorney, Agent, or Firm* — Dann, Dorfman, Herrell and Skillman, P.C.

(57) ABSTRACT

A system and method for the detection of bacteria on a sample, utilizes spectroscopic analysis of the sample and the fluorescent properties of bacteria or other substance(s) or matter associated with the bacteria to identify the presence of bacteria on the sample. A detector analyses light emitted from the sample in response to illumination. The detector 5 is arranged to analyze the emission spectra across two wavebands, a first waveband containing the wavelengths associated with the fluorescent properties of the bacterial species or other substance or matter to be detected, and a second waveband excluding these wavelengths but also having an overlapping region with the first waveband.

16 Claims, 3 Drawing Sheets

(51) Int. Cl.
*C12Q 1/04* (2006.01)
*G01J 3/36* (2006.01)
*G01J 3/42* (2006.01)
*G01J 3/02* (2006.01)
G01N 33/12 (2006.01)
G01N 21/63 (2006.01)

(52) U.S. Cl.
CPC .............. *G01J 3/42* (2013.01); *G01N 21/645* (2013.01); *G01N 21/6486* (2013.01); *G01N 33/12* (2013.01); *G01N 2021/635* (2013.01); *G01N 2021/6417* (2013.01); *G01N 2021/6484* (2013.01); *G01N 2201/0612* (2013.01)

(56) References Cited

U.S. PATENT DOCUMENTS

| 7,468,520 B1 | 12/2008 | Varmette et al. |
| 2003/0160231 A1 | 8/2003 | Cole et al. |

OTHER PUBLICATIONS

CN Appln. No. 2013800408620; Second Chinese Examination Report, dated Mar. 24, 2017, pp. 3-5 (Chinese national phase of PCT/NZ2013/000094).

* cited by examiner

REAL TIME OPTICAL DETECTION OF BACTERIA

FIELD OF THE INVENTION

The invention relates to detection and enumeration of bacteria, and in particular to a spectroscopic method, system and device for detection of bacteria on meat surfaces.

BACKGROUND OF THE INVENTION

Early-detection and elimination of food-borne bacteria is essential for extending retailer shelf life and preventing consumer impact. Spectroscopic devices for determining the freshness of meat by relying on the fluorescent properties of bacteria species are known. In such devices, a sample is typically exposed to a light signal having a certain excitation wavelength, and a light detector detects emitted light of a longer wavelength (fluorescence) from the sample to identify the presence of bacteria. Spectroscopy is often real time, non invasive, non-destructive and non-chemical. Through careful examinations of excitation and emission spectra of bacteria one can construct 'fingerprints' for bacterial species detection and identification. It is also possible to estimate the level of bacterial contamination as the emission intensity is proportional to the bacterial concentration.

Known bacteria detection devices utilise narrowband filters to isolate and analyse the fingerprint wavelengths in the emitted signal. Narrowband filters are generally more expensive and have a larger attenuation factor than their long pass counterpart.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide a spectroscopic method, system or device for detection of bacteria that goes in some way towards alleviating some of the disadvantages of known devices as listed above, or to at least provide the public with a useful choice.

SUMMARY OF THE INVENTION

In a first aspect the invention may broadly be said to consist of a method for detecting the presence of bacteria in or on an illuminated sample, the method comprising the steps of:
  receiving a first signal indicative of intensity of light emitted from the sample across a first waveband, the first waveband containing one or more wavelengths associated with the fluorescent properties of the bacteria to be detected,
  receiving a second signal indicative of intensity of light emitted from the sample across a second waveband excluding the one or more wavelengths associated with the fluorescent properties of the bacteria, said first and second wavebands having overlapping regions,
  comparing the first signal to the second signal, and
  identifying the presence of a bacterial species when an output of the comparison conforms with a predetermined threshold criteria.

Preferably the step of comparing the first signal to the second signal comprises:
  determining a first value indicative of a strength of the first signal,
  determining a second value indicative of a strength of the second signal, and
  dividing the first value by the second value, and wherein the presence of the bacterial species is identified when the output of the division is above a predetermined threshold.

Preferably the steps of determining the first and second values comprise integrating the first and second signals over the first and second wavebands respectively.

Preferably the method further comprises prior to receiving the first and second signals, the steps of:
  illuminating the sample with light at an excitation wavelength outside the first and second wavebands,
  receiving light emitted from the sample in response to the illumination, and
  filtering the emitted light into first and second filtered light signals within the first and second wavebands respectively.

Preferably the first waveband has a shorter lower band limit wavelength than the second waveband.

Preferably the excitation wavelength is shorter than the lower band limit wavelength of the first waveband.

The sample may be a meat, vegetable or fruit sample. Alternatively the sample is a non-living sample or surface such as a bench, tool or other equipment.

In a first embodiment the bacterial species is *pseudomonas*. Alternatively, or in addition, the bacterial species is *E. Colli*.

Preferably the sample is a meat sample.

Preferably the excitation wavelength is approximately 405 nm.

Preferably the first waveband is approximately 450-800 nm and the second waveband is approximately 580-800 nm.

In an alternative embodiment the bacterial species is *Pseudomonas syringae* pv. Actinidiae.

Preferably the sample is a fruit sample.

Preferably the excitation wavelength is approximately 430 nm.

Preferably the lower cut-off limit of the first waveband is approximately 600 nm and the lower cut-off limit of the second waveband is approximately 850 nm.

In a second aspect the invention may broadly be said to consist of a device for detecting the presence of bacteria on a sample, the device comprising:
  a memory component for storing data indicative of a predetermined threshold criteria associated with the bacteria, and
  a processor configured to:
  receive a first signal indicative of intensity of light emitted from the sample across a first waveband, the first waveband containing one or more wavelengths associated with the fluorescent properties of the bacteria to be detected,
  receive a second signal indicative of intensity of light emitted from the sample across a second waveband excluding the one or more wavelengths associated with the fluorescent properties of the bacteria, said first and second wavebands having overlapping regions,
  compare the first signal to the second signal, and
  identify the presence of a bacteria when an output of the comparison conforms with the predetermined threshold criteria stored in memory.

Preferably the processor is configured to compare the first signal to the second signal by dividing a first value indicative of a strength of the first signal by a second value indicative of a strength of the second signal, and wherein the presence of the bacteria is identified by the processor when the output of the division is above a predetermined threshold.

Preferably the first waveband has a shorter lower band limit wavelength than the second waveband.

Preferably the excitation wavelength is shorter than the lower band limit wavelength of the first waveband.

Preferably the device further comprises:
a first longpass filter arranged to filter a light beam and having a first operative waveband, and
a second longpass filter arranged to filter a light beam and having a second operative waveband, wherein the first and second wavebands have different lower cut-off limit wavelengths and overlap.

Preferably the device further comprises first and second photomultiplier tubes adjacent the first and second filters respectively, for receiving filtered light beams from the first and second filters and outputting the first and second signals indicative of light intensities to the processor respectively.

Preferably the device further comprises a beam splitter adjacent the first and second filters and arranged to receive a light beam and split the beam into two beams traversing in different directions towards the first and second filters respectively.

Preferably the device further comprises a light source for generating a beam of light.

Preferably the device further comprises an optical fibre cable coupled to the light source for transmitting light out of the device and onto the sample.

Preferably the cable comprises a fibre bundle for transmitting light from the detector to the sample and receiving light from the sample back to the detector. Preferably the bundle comprises a central excitation fibre for transmitting light from the light source to the sample to thereby illuminate the sample, and an array of emission fibres surrounding the central excitation fibre for transmitting light emitted from the sample in response to illumination to the detector.

Preferably the excitation fibre is optically coupled to the light source, the emission fibres are optically coupled to the beam splitter, and the cable is optically coupled to a lens element adjacent the sample.

Preferably the lens is arranged to yield an excitation light beam from the central excitation fibre onto a region of interest on the sample in one direction and yield an emission light beam emitted from the sample into the emission fibres in an opposite direction.

The sample may be a meat, vegetable or fruit sample. Alternatively the sample is a non-living sample or surface such as a bench, tool or other equipment.

In a first embodiment the bacterial species is *pseudomonas*. Alternatively, or in addition, the bacterial species includes *E. Colli*.

Preferably the sample is a meat sample.

Preferably the excitation wavelength is approximately 405 nm.

Preferably the lower cut-off limit of the first waveband is approximately 450 nm and the lower cut-off limit of the second waveband is approximately 580 nm.

In an alternative embodiment the bacterial species is *Pseudomonas syringae* pv. Actinidiae.

Preferably the sample is a fruit sample.

Preferably the excitation wavelength is approximately 430 nm.

Preferably the lower cut-off limit of the first waveband is approximately 600 nm and the lower cut-off limit of the second waveband is approximately 850 nm.

In a third aspect the invention may broadly be said to consist of a system for detecting the presence of bacteria on a sample, the system comprising:
a light source for illuminating the sample with excitation light, and
a light detector for detecting the presence of bacteria based on light emitted from the sample after illumination, the detector having:
a memory component for storing data indicative of a predetermined threshold criteria associated with the bacteria, and
a processor configured to:
receive a first signal indicative of intensity of light emitted from the sample across a first waveband, the first waveband containing one or more wavelengths associated with the fluorescent properties of the bacteria to be detected,
receive a second signal indicative of intensity of light emitted from the sample across a second waveband excluding the one or more wavelengths associated with the fluorescent properties of the bacteria, said first and second wavebands having overlapping regions,
compare the first signal to the second signal, and
identify the presence of a bacteria when an output of the comparison conforms with the predetermined threshold criteria stored in memory.

Preferably the processor is configured to compare the first signal to the second signal by dividing a first value indicative of a strength of the first signal by a second value indicative of a strength of the second signal, and wherein the presence of the bacteria is identified by the processor when the output of the division is above a predetermined threshold.

Preferably the first waveband has a shorter lower band limit wavelength than the second waveband.

Preferably the excitation wavelength is shorter than the lower band limit wavelength of the first waveband.

Preferably the device further comprises:
a first longpass filter arranged to filter a light beam and having a first operative waveband, and
a second longpass filter arranged to filter a light beam and having a second operative waveband, wherein the first and second wavebands have different lower cut-off limit wavelengths and overlap.

Preferably the light detector further comprises first and second photomultiplier tubes adjacent the first and second filters respectively, for receiving filtered light beams from the first and second filters and outputting the first and second signals indicative of light intensities to the processor respectively.

Preferably the light detector further comprises a beam splitter adjacent the first and second filters and arranged to receive a light beam and split the beam into two beams traversing in different directions towards the first and second filters respectively.

Preferably the system further comprises one or more optical fibre cables optically coupled to the light source for transmitting excitation light out of the device and onto the sample, and optically coupled to the detector for transmitting emitted light from the sample to the detector.

Preferably the system comprises one cable having a fibre bundle for transmitting excitation light from the light source to the sample and receiving emission light from the sample back to the detector. Preferably the bundle comprises a central excitation fibre for transmitting excitation light from the light source to the sample to thereby illuminate the sample, and an array of emission fibres surrounding the central excitation fibre for transmitting light emitted from the sample in response to illumination to the detector.

Preferably the excitation fibre is optically coupled to the light source, the emission fibres are optically coupled to the beam splitter of the detector.

Preferably the system further comprises a lens optically coupled to the cable on one side and to the sample on the other side.

Preferably the lens is arranged to yield an excitation light beam from the central excitation fibre onto a region of interest on the sample in one direction and yield an emission light beam emitted from the sample into the emission fibres in an opposite direction.

In a first embodiment the bacterial species is *pseudomonas*. Alternatively or in addition the bacterial species includes *E. Colli*.

Preferably the sample is a meat sample.

Preferably the excitation wavelength is approximately 405 nm.

Preferably the lower cut-off limit of the first waveband is approximately 450 nm and the lower cut-off limit of the second waveband is approximately 580 nm.

In an alternative embodiment the bacterial species is *Pseudomonas syringae* pv. Actinidiae.

Preferably the sample is a fruit sample.

Preferably the excitation wavelength is approximately 430 nm.

Preferably the lower cut-off limit of the first waveband is approximately 600 nm and the lower cut-off limit of the second waveband is approximately 850 nm.

In a fourth aspect the invention may broadly be said to consist of a method for detecting the presence of a substance in or on an illuminated sample, the method comprising the steps of:
  receiving a first signal indicative of intensity of light emitted from the sample across a first waveband, the first waveband containing one or more wavelengths associated with the fluorescent properties of the substance to be detected,
  receiving a second signal indicative of intensity of light emitted from the sample across a second waveband excluding the one or more wavelengths associated with the fluorescent properties of the substance, said first and second wavebands having overlapping regions,
  comparing the first signal to the second signal, and
  identifying the presence of the substance when an output of the comparison conforms with a predetermined threshold criteria.

The sample may be a meat, vegetable or fruit sample. Alternatively the sample is a non-living sample or surface such as a bench, tool or other equipment.

In a first embodiment, the substance is bacteria.

Preferably the bacterial species is *pseudomonas*. Alternatively, or in addition, the bacterial species includes *E. Colli*.

Preferably the sample is a meat sample.

Preferably the excitation wavelength is approximately 405 nm.

Preferably the lower cut-off limit of the first waveband is approximately 450 nm and the lower cut-off limit of the second waveband is approximately 580 nm.

In a second embodiment, the substance is Chlorophyll, or metabolites of Chlorophyll or both.

The sample may be a meat, vegetable or fruit sample.

Preferably the excitation wavelength is between approximately 350 nm and 650 nm. The excitation wavelength may be approximately 365 nm or approximately 405 nm or approximately 450 nm or approximately 635 nm or approximately 650 nm.

Most preferably the excitation wavelength is approximately 450 nm.

Preferably a lower cut-off limit of the first waveband is approximately 650 nm and a lower cut-off limit of the second waveband is approximately 720 nm.

In a fifth aspect the invention may broadly be said to consist of a method for detecting the presence of bacteria in or on an illuminated sample, the method comprising the steps of:
  receiving a first signal indicative of intensity of light emitted from the sample across a first waveband, the first waveband containing one or more wavelengths associated with the fluorescent properties of the bacteria or a substance associated with the bacteria to be detected,
  receiving a second signal indicative of intensity of light emitted from the sample across a second waveband excluding the one or more wavelengths associated with the fluorescent properties, said first and second wavebands having overlapping regions,
  comparing the first signal to the second signal, and
  identifying the presence of the bacteria when an output of the comparison conforms with a predetermined threshold criteria.

Preferably the first signal to the second signal comprises:
  determining a first value indicative of a strength of the first signal,
  determining a second value indicative of a strength of the second signal, and
  dividing the first value by the second value, and wherein the presence of the bacteria is identified when the output of the division is above a predetermined threshold.

Preferably the steps of determining the first and second values comprise integrating the first and second signals over the first and second wavebands respectively.

Preferably the method further comprises, prior to receiving the first and second signals, the steps of:
  illuminating the sample with light at an excitation wavelength outside the first and second wavebands,
  receiving light emitted from the sample in response to the illumination, and
  filtering the emitted light using the first waveband to obtain the first signal, and
  filtering the emitted light using the second waveband to obtain the second signal.

Preferably the first waveband has a shorter lower band limit wavelength than a lower band limit wavelength of the second waveband.

Preferably the excitation wavelength is shorter than or equal to the lower band limit wavelength of the first waveband.

The sample may be a meat, vegetable or fruit sample. Alternatively the sample is a non-living sample or surface such as a bench, tool or other equipment.

In a first embodiment the first waveband contains one or more wavelengths associated with the fluorescent properties of the bacteria, and the bacteria is *pseudomonas*.

Preferably the illuminated sample is a meat sample.

Preferably the excitation wavelength is approximately 405 nm.

Preferably a lower cut-off limit of the first waveband is approximately 450 nm and a lower cut-off limit of the second waveband is approximately 500 nm. Preferably the first waveband is between approximately 450 nm and 800 nm and the second waveband is between approximately 500 nm and 800 nm.

In a second embodiment the first waveband contains one or more wavelengths associated with the fluorescent properties of a substance associated with the bacteria, and wherein the substance is Chlorophyll or metabolites of Chlorophyll or both.

The sample may be a meat, vegetable or fruit sample.

Preferably the excitation wavelength is between approximately 350 nm and 650 nm. The excitation wavelength may be approximately 365 nm or approximately 405 nm or approximately 450 nm or approximately 635 nm or approximately 650 nm.

Most preferably the excitation wavelength is approximately 450 nm.

Preferably a lower cut-off limit of the first waveband is approximately 650 nm and a lower cut-off limit of the second waveband is approximately 720 nm.

In a sixth aspect the invention may broadly be said to consist of a device for detecting the presence of bacteria on a sample, the device comprising:
  a memory component for storing data indicative of a predetermined threshold criteria associated with the bacteria or associated with a substance indicative of the bacteria, and
  a processor configured to:
  receive a first signal indicative of intensity of light emitted from the sample across a first waveband, the first waveband containing one or more wavelengths associated with the fluorescent properties of the bacteria or the substance,
  receive a second signal indicative of intensity of light emitted from the sample across a second waveband excluding the one or more wavelengths associated with the fluorescent properties of the bacteria, said first and second wavebands having overlapping regions,
  compare the first signal to the second signal, and
  identify the presence of a bacteria when an output of the comparison conforms with the predetermined threshold criteria stored in memory.

In a seventh aspect the invention may broadly be said to consist of a system for detecting the presence of bacteria on a sample, the system comprising:
  a light source for illuminating the sample with excitation light, and
  a light detector for detecting the presence of bacteria based on light emitted from the sample after illumination, the detector having:
    a memory component for storing data indicative of a predetermined threshold criteria associated with the bacteria or with a substance associated with the bacteria, and
    a processor configured to:
      receive a first signal indicative of intensity of light emitted from the sample across a first waveband, the first waveband containing one or more wavelengths associated with the fluorescent properties of the bacteria or the substance,
      receive a second signal indicative of intensity of light emitted from the sample across a second waveband excluding the one or more wavelengths associated with the fluorescent properties of the bacteria or the substance, said first and second wavebands having overlapping regions,
      compare the first signal to the second signal, and
      identify the presence of a bacteria when an output of the comparison conforms with the predetermined threshold criteria stored in memory.

It will be appreciated any one or more of the above aspects can be provided in combination with any one or more of the above preferred or alternative embodiments or features.

The term "longpass" when used in this specification and claims in relation to filters, wavebands, passbands or any other spectral component means the attenuation of relatively shorter wavelengths and transmission of relatively longer wavelengths over the active region of the target spectrum. The term "longpass" includes wide bandpass but not narrowband filters or wavebands.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF PREFERRED EMBODIMENTS

1. Bacteria Detection System

Figure 1:
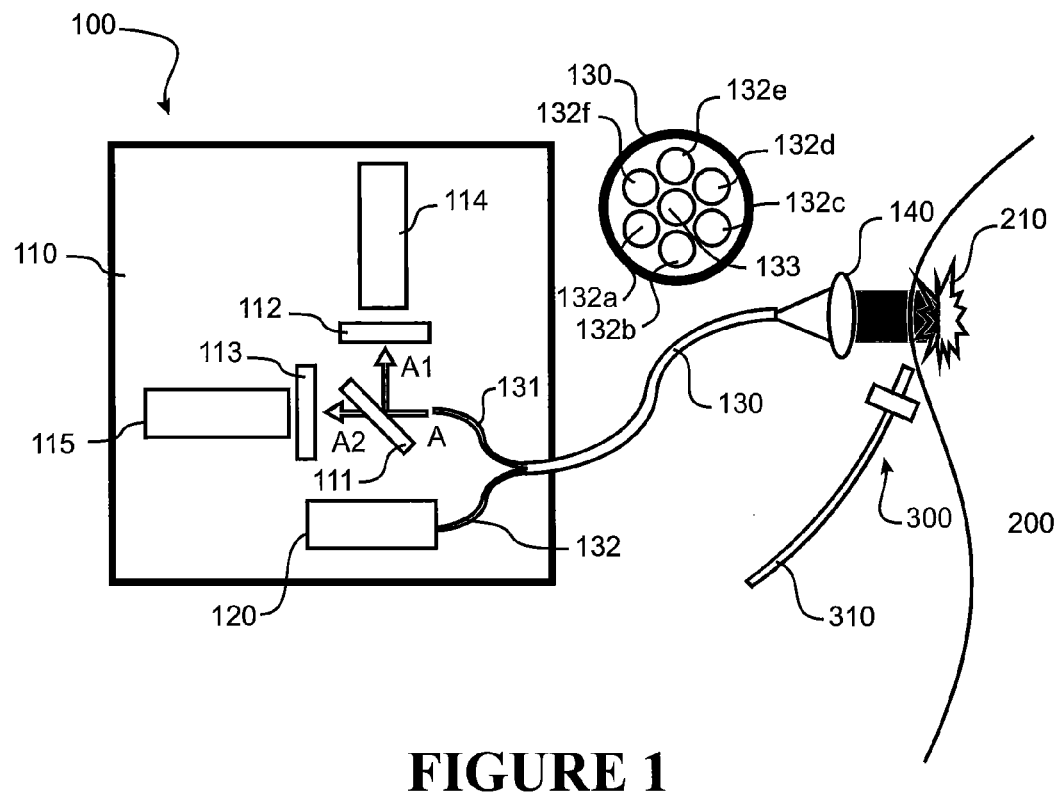
FIG. 1 is a schematic of showing the components of a preferred form bacteria detection system of the invention.

Referring to FIG. 1, a schematic of a preferred form bacteria detection system 100 of the invention is shown. The system 100 comprises a bacteria detection device 110 (hereinafter "detector" 100), a light source 120, a light transmission medium 130 and a collimating lens 140. The system 100 is spectroscopic and utilises the fluorescent properties of bacteria or other substance(s) or matter to identify the presence of one or more bacterial species within or on a sample or target product 200. The system 100 operates by illuminating the sample 200 using a light beam from the light source 120, and analysing at the detector 110 light emitted from the sample 200 in response to the illumination. The light transmission medium 130 provides optical communication between the light source and the sample, and between the sample and the detector. In the preferred embodiment, the light transmission medium 130 is an optical fibre cable 130 and more preferably a cable comprising a fibre bundle as will be explained in more detail further. A sample 200 to be analysed is positioned adjacent the lens 140 to yield an excitation beam onto the area 210 of the sample to be analysed. The lens in the preferred embodiment also receives light emitted from the sample and yields an emission beam it in the opposite direction towards the detector 110 for analysis.

The sample 200 may be from a living or non-living species or surface. For example, as in the case of the preferred embodiments, the sample is from a living species such as a meat sample, a fruit sample or a vegetable sample. Alternatively the sample 200 may be or may be from a non-living surface or structure such as a bench, tool, piece of equipment or any other non-living surface where the detection of bacteria may be desirable.

The detector 110 is arranged to receive light emitted from the illuminated region 210 of the sample 200 and analyse the emission spectra to determine the presence of bacteria, by preferably identifying the presence of one or more bacterial species, or alternatively identifying the presence of one or more other substances or matter indicative of the presence of bacteria or associated with the presence of bacteria. The detector 110, in particular, is arranged to analyse the spectra across two wavebands, a first waveband containing the wavelengths associated with the fluorescent properties of the bacterial species or other substance or matter to be detected, and a second waveband excluding these wavelengths but also having an overlapping region with the first waveband. By comparing the spectral intensities of the emitted light across the two wavebands, the detector 110 is able to identify the presence of the one or more bacterial species or other substance or matter 200.

The methods and systems described for this invention are not intended to be limited to any particular application. The preferred embodiment predominantly used to describe the features of the invention is the detection of bacteria on meat or other food samples. However, it will be appreciated that the method and system for detection can be applied in various alternative applications to detect the presence of any species or substance or matter on a sample that exhibits fluorescent properties when the sample is illuminated.

Such alternative applications are not intended to be excluded from the scope of the invention.

1.1. Detector

A schematic of a preferred form detector 110 of the invention is shown in FIG. 1. The detector 110 comprises a beam splitter 111, two filters 112 and 113, and two photomultiplier tubes (PMTs) 114 and 115 associated with the filters.

The detector 110 is configured to receive light emitted from the illuminated region 210 of the sample 200. In the preferred embodiment, light is transmitted by the system 100 using optical cable 130 having an emission light branch 131 that is optically coupled with the beam splitter 111 of the detector 110. The cable 130 is preferably fixedly coupled to the detector 110 adjacent the beam splitter 111 for transmitting emitted light to the beam splitter 111.

During operation, light emitted from the sample 200 (in response to illumination), traverses through the optical cable 130 towards the detector 110 and through branch 131 where it meets the beam splitter 111. The beam splitter 111 splits the beam of light A at the output of the branch 131 into two beams A1 and A2 travelling in different directions. The beam splitter 111 may be formed using any one of a number of designs known in the art of optics.

Adjacent the splitter 111 are two optical filters, 112 and 113, configured to be in the optical paths of the output beams of the beam splitter 111. The filters 112 and 113 have different optical characteristics. In other words, filter 112 is arranged to selectively transmit light within a first waveband, and filter 113 is arranged to selectively transmit light within a second waveband different from the first. In the preferred embodiment, both filters 112 and 113 are longpass filters having a lower limit cut-off wavelength that is longer than (or substantially equal to) the wavelength of the excitation beam transmitted from the light source 120. Filter 112 includes the one or more wavelengths associated with the fluorescent properties of the bacterial species or other substance or matter to be identified in its passband and filter 113 does not. In other words, filter 113 has a lower limit cut-off wavelength that is longer than the one or more wavelengths associated with the fluorescent properties of the bacterial species or other substance or matter.

Figure 2:
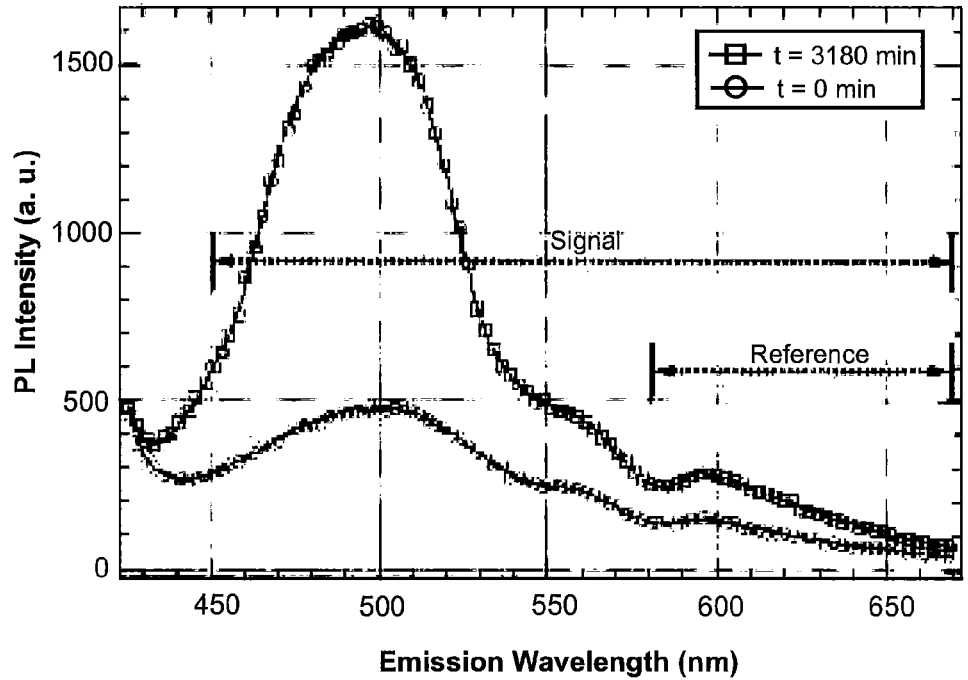
FIG. 2 is a graph showing the emission spectra of *Pseudomonas* in a 13 day old meat sample immediately after unpacking and after 53 hours at room temperature.

Referring to FIG. 2, for example, in a preferred embodiment, the detector 110 is arranged to detect the presence of *Pseudomonas* bacteria. *Pseudomonas,* when excited by light at approximately 405 nm, fluoresces and emits light at approximately 497 nm. Filters 112 and 113 in this preferred embodiment therefore have lower limit cut-off wavelengths that are longer than 405 nm, and further filter 113 has a lower limit cut-off wavelength that is longer than 497 nm. In this preferred embodiment, filter 112 has a lower cut-off limit of 450 nm ('signal' spectrum), while filter 113 has a lower cut-off limit of 580 nm ('reference' spectrum).

Figure 6:
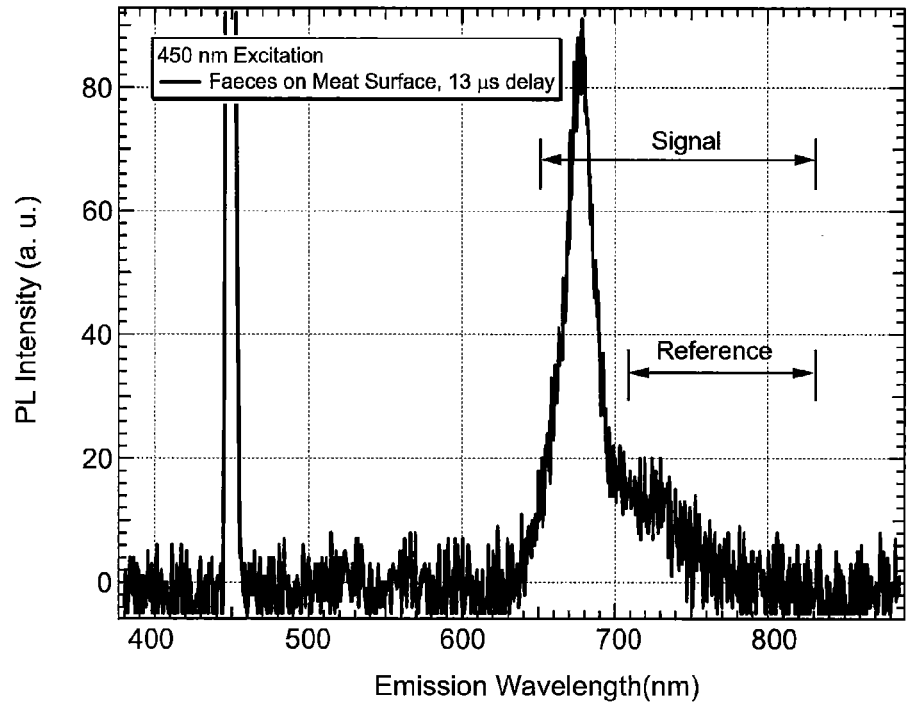
FIG. 6 is a graph showing the emission spectra of faecal matter of the second embodiment after a detection delay of 13 µs.

Referring to FIG. 6, for example, in another preferred the detector 110 is arranged to detect the presence of faecal matter on the surface of a meat, fruit or vegetable sample 200. The presence of faecal matter is indicative of the presence of one or more bacterial species on the sample 200. Chlorophylls and their metabolites are present in the faecal matter of plant eating animals and exhibit fluorescent properties when exited by light. Chlorophyll is therefore a suitable indicator for the inspection and identification of faecal contamination and can be associated with the presence of bacteria on such samples/foods 200. Chlorophyll or the metabolites of Chlorophyll fluoresce with a spectral waveband of approximately 650-750 nm when excited by light having a wavelength between 350 nm and 650 nm. In this embodiment, filters 112 and 113 have lower limit cut-off wavelengths that are longer than or equal to 650 nm. Filter 112 has a lower limit cut-off wavelength of approximately 650 nm ('signal' spectrum) and filter 113 has a cut-off wavelength of approximately 720 nm ('reference' spectrum).

It will be appreciated that for different bacteria, substance, sample and/or applications different cut-off frequencies may be used for the filters 112 and 113 without departing from the scope of the invention. Photoluminescent (PL) intensities of emitted light can be weak, especially when the light is collected from a relatively great distance from the sample. Narrowband filters make light emission detection difficult in the presence of weak intensities. The use of longpass filters (as opposed to narrowband filters) enhances detection of the emitted light.

Referring back to FIG. 1, the light transmitted from filters 112 and 113 is then input into two respective PMTs 114 and 115. The tubes 114/115 have the function of outputting electrical energy in response to input optical energy. In other words, PMTs 114 and 115 convert the received light beams transmitted from filters 112 and 113 into current signals. The PMTs may then process the current signals or output the signals for external processing. In the preferred embodiment the PMTs 114/115 determine a voltage value indicative of the strength of the current signal across its respective spectrum. The voltages output by the PMTs 114/115 are utilised and compared by a processor associated with the detector 110 to detect the presence of bacteria or other species, substance or matter.

Referring again to FIGS. 2 and 6, each PMT 114/115 will convert the PL intensity spectrum received from the respective filter 112/113 into indicative current signals. The two current signals are received by the processor and compared to determine the presence of bacteria, Chlorophyll or other substance or matter. In the preferred embodiment, each PMT 114/115 after converting the associated PL intensity spectrum into a current signal determines an integral of the signal across its associated waveband. This results in a voltage output for a processor to compare and then detect the presence of bacteria, Chlorophyll or other substance or matter based on the comparison. In the preferred embodiment, the processor determines a ratio of the two voltages output from the two PMTs 114/115. This ratio is compared against a predetermined threshold criterion indicative of the presence of the bacteria, Chlorophyll, or other substance or matter to be identified. In the first preferred embodiment of FIG. 2, equation 1 below is utilised to analyse the current signals of the PMTs 114/115 and detect the presence of bacteria:

$$\text{Detector output} \approx \frac{\int_{450}^{670} PL(\lambda)R(\lambda)d\lambda}{\int_{580}^{670} PL(\lambda)R(\lambda)d\lambda} = \frac{V_{sig}}{V_{ref}}, \quad (1)$$

In the second preferred embodiment, equation 2 below is utilised to analyse the current signals of the PMTs 114/115 and detect the presence of Chlorophyll/faecal matter:

$$\text{Output}_{Detector} \approx \frac{\int_{650}^{800} PL(\lambda)R(\lambda)d\lambda}{\int_{720}^{800} PL(\lambda)R(\lambda)d\lambda} = \frac{V_{sig}}{V_{ref}} \quad (2)$$

In general, equation 2 below is utilised to analyse the current signals of the PMTs 114/115 and detect the presence of the bacteria, Chlorophyll or other substance or matter to be identified in the sample:

$$\text{Output}_{Detector} \approx \frac{\int_{S_{min}}^{S_{max}} PL(\lambda)R(\lambda)d\lambda}{\int_{R_{min}}^{R_{max}} PL(\lambda)R(\lambda)d\lambda} = \frac{V_{sig}}{V_{ref}} \quad (3)$$

Where PL is the PL intensity determined by the respective PMT, R is wavelength-dependent response level (A/W) of the PMTs 114/115 and $V_{sig}$ and $V_{ref}$ are the output voltages converted by each PMT. The limits of the integration are given by operative waveband of the optical filters 112/113 used in the detection and by the practical limit of the associated components (such as the PMTs 114/115) of the detector 110. In other words, $S_{min}$ and $S_{max}$ are the lower and upper limit cut-off wavelengths of the first filter 112 and $R_{min}$ and $R_{max}$ are the lower and upper limit cut-off wavelengths of the second filter 113, It will be appreciated that an alternative method of comparison of the PL intensities output from the filters 112/113 can be used to detect the presence of bacteria, Chlorophyll, or other substance or matter as required by the particular application and the invention is not intended to be limited to the above preferred method.

Furthermore, the processing of the PL intensities can be done across one or more components of the system 100. In the preferred embodiment, PMTs 114 and 115 are used to convert the PL beams into electrical signals and in particular into absolute voltages indicative of the strength of the signal across the respective spectrum. An external processor whether housed within the detector 110 or remote receives and compares the voltage signals ($V_{sig}$ and $V_{ref}$) output from the PMTs to detect the presence of bacteria, Chlorophyll or other substance or matter. In an alternative embodiment, the PMTs 114/115 may output current signals, the spectrums of which are analysed by an external processor (through integration for example) to determine the presence of bacteria Chlorophyll or other substance or matter.

In the preferred embodiment, the detector 110 is configured to operate in real time. The detector 110 is configured to receive, filter and process the light emitted from the illuminated region 210 of the sample 200 in real time or near real time with minimal delay from time of excitation. The method utilised by the processor to analyse the electronic signals associated with the two filtered light beams does not require high processing capability or resource consumption and is therefore well suited for real time or near real time detection and related applications. Such a detector 110 can therefore be used in a multitude of applications where real time detection is necessary or highly beneficial such as in the food product industries where a large number of products may need to be examined for bacteria and transported to another location quickly and efficiently.

In a first preferred embodiment, the detector is configured to determine the presence of bacteria on meat products and in particular the presence of any one or more of *Pseudomonas, E. Coli, Bacillus Subtilis* and *Bacillus* spores. The detector 110 may therefore comprise one or more beam splitters, filter pairs and PMT pairs with operating characteristics as will be required to determine the presence of the one or more bacterial species. Differentiation in bacteria species may be achieved by adding a filter wheel to select different detecting region for other bacteria species. Alternatively or in addition, modulating current of the light source 120 and gating detector 110 will provide further differentiation of bacteria as life times of excited state of molecules in bacteria are slightly different depending on the microbial environment.

In one embodiment, the detector 110 is configured to detect the presence of *E. Coli* bacteria. In such an embodiment, a light source 120 producing a light beam with an excitation wavelength of approximately 405 nm is utilised to illuminate the sample 200. *E. Coli* fluoresces with a relatively broad spectrum around 500 nm so the detector may comprise a first long pass filter 112 having a cut-off wavelength of approximately 450 nm and a second long pass filter having a cut-off wavelength of approximately 600 nm.

It another embodiment, the detector 110 is configured to detect the presence of *Pseudomonas Syringae* in a fruit sample 200, and in particular *Pseudomonas Syringae* pv. Actinidiae in a kiwifruit sample 200. *Pseudomonas syringae* pv. Actinidiae fluoresces with a spectral waveband of approximately 650-750 nm. In such an embodiment, a light source 120 producing a light beam with an excitation wavelength of approximately 430 nm is utilised to illuminate the sample 200. The detector may comprise a first long pass filter 112 having a cut-off wavelength of approximately 600 nm and a second long pass filter having a cut-off wavelength of approximately 850 nm.

Referring to FIG. 6, in a second preferred embodiment, the detector 110 is configured to detect the presence of faecal matter on the surface of a meat, fruit or vegetable sample 200. Faecal matter on food products is indicative of the presence of bacteria. Chlorophylls and their metabolites are present in the faecal matter of plant eating animals and are suitable markers for the inspection and identification of faecal contamination on such samples/foods 200. Faecal contamination is the major source of microbial contamination on meat, fruit and vegetable. Chlorophyll and/or the metabolites of Chlorophyll fluoresce with a spectral waveband of approximately 650-750 nm. In such an embodiment, a light source 120 producing a light beam with a continuous or modulated excitation wavelength of approximately between 350 nm and 650 nm is utilised to illuminate the sample 200. The light beam may comprise an excitation wavelength of approximately 365 nm, approximately 405 nm, approximately 450 nm, or approximately 650 nm. The excitation wavelength is most preferably 450 nm. The detector may comprise a first long pass filter 112 having a cut-off wavelength of between approximately 650 nm and 670 nm and a second long pass filter 113 having a cut-off wavelength of between approximately 720 nm and 750 nm. The first low pass filter 113 preferably has a cut-off wavelength of approximately 650 nm but may alternatively have a cut-off wavelength of approximately 670 nm. The second long pass filter preferably has a cut-off wavelength of approximately 720 nm but may alternatively have a cut-off wavelength of approximately 750 nm.

Figure 5:
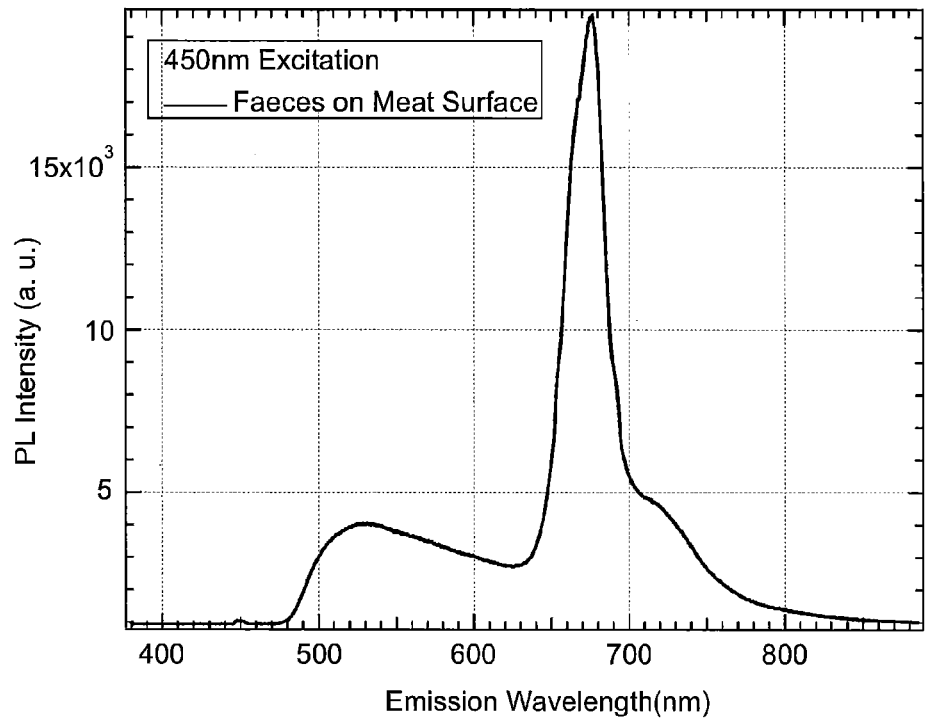
FIG. 5 is a graph showing the emission spectra of faecal matter in accordance with a second preferred embodiment of the invention, without any detection delay.

In any one of the above embodiments, the detector may receive continuous, real-time or delayed optical signals. Delayed detection can be achieved by a mechanical chopper or an electronically gated system. In the second preferred embodiment, delayed detection can eliminate strong broad meat emission which only occurs for a short period of time following excitation and will single out relatively narrow faecal emission for example. Referring to FIGS. 5 and 6, it can be seen that without a delay, the broad meat emission dominates the emission signal. Applying a detection delay of 13 µs following excitation substantially eliminates this strong broad meat emission allowing the faecal emission to be more easily detected. The applied delay may be anywhere between 1 µs and 1 ms, more preferably between 5 µs and 50 µs and most preferably between 10 µs and 15 µs.

In some embodiments, photon counting can be used to collect output signals from the detector. In such embodiments, a lock-in amplifier can be used to single out the AC component of a detected signal when the excitation wavelength is modulated.

1.2. Light Source

The light source 120 is any device capable of producing light of one or more excitation wavelengths as required by the particular application. The lights source 120 may be a diode laser configured to output an excitation beam at a wavelength of approximately 405 nm. The light source may be polarised in a particular orientation to optimise emission. The 405 nm light beam is particularly advantageous in meat applications, and in particular for bacteria detection via bacteria emission as in the first preferred embodiment above, since it does not significantly excite fat while exciting Flavin containing fluorophores which are responsible for bacteria emission. The light source may, alternatively or in addition, output an excitation light beam at a wavelength of approximately 450 nm or 650 nm, or anywhere between approximately 350 nm and 650 nm in accordance with other embodiments of the invention as described above. The mode of operation of the light source 120 can be continuous, modulated or pulsed.

The light source 120 may be housed within the detector 110 as shown in the preferred embodiment, or alternatively separate from the detector 110. The light source 120 is in optical communication with the lens 140 adjacent the sample 200 through the excitation branch 132 of optical fibre cable 130.

It will be appreciated that alternative light sources and excitation wavelengths may be used as required by the particular application. The light source 120 may be configured to output one or more excitation light beams.

It will be also appreciated that the power of the light source 120 may be varied during detection. The power can be varied either by changing the current level to the light source 120 or placing neutral density filters in the optical paths of the light source 120.

1.3. Light Transmission Medium

As previously described, the preferred form optical transmission medium 130 is an optical fibre cable 130 having a branched end 131/132 for optically coupling the detector 110 and the light source respectively. The cable 130 at the other end optically couples the region 210 of the sample 200 to be analysed through the lens 140.

In the preferred form, the optical cable 130 comprises a bundle of optical fibres 132a-f and 133. These fibres 132/133 are configured to allow the cable to separately transmit excitation and emission beams. In particular, the preferred form cable 130 comprises a central excitation fibre element 133 surround by an array of emission fibre elements 132a-f. It will be appreciated that the number and distribution of the fibre elements within the cable 130 may be different in alternative embodiments. Excitation light from the light source 120 travels through the excitation fibre 133 to the lens 140 where it is projected onto the region 210 to be analysed. Light emitted from the region is projected by the lens 140 into the surrounding array of fibre elements 132a-f to then be transmitted through the cable 130 to the beam splitter 111 of the detector 110.

In the preferred embodiment, the collimating lens 140 is configured at the sample end of the optical fibre cable 130 to yield an excitation beam of approximately 1 cm diameter.

It will be appreciated that the properties of the lens depends on the sampling area required for the particular application.

An additional Galvano mirror system can be attached near the lens 140 to expand the area of sampling. Polarisers may be installed in some embodiments at the head of the medium 130 to provide the collection of preferable polarisations only.

2. Experimentation 2.1. Setup

For this study the light dispersing element is omitted as it is not of interest to resolve bacteria emission but to detect signal. It will be appreciated in some embodiments of the invention a light dispersing element may be utilised. Two identical photomultiplier tubes (PMTs) 114/115 were employed; each of which were specifically designated in detecting signal and reference, respectively. A 405 nm diode laser 120 was used. The 405 nm is advantageous since it does not significantly excite fat while exciting Flavin containing fluorophores which are responsible for bacteria emission. Raman signal of water residue on meat surface is expected at ~470 nm or equivalently 3400 $cm^{-1}$ which is below the detecting peak wavelength of 497 nm. False detection due to water is then expected to be suppressed.

Optical excitation from the laser 120 is delivered through a fibre bundle 130. A collimating lens 140 was used in one end of the fibre to yield a beam with diameter of ~1 cm which is equivalent to sampling area. Bacteria emission is then collected from the same lens 140 in a backscattering geometry as shown in FIG. 1 and delivered to the other end of the bundle 131. A BK7 beam splitter 111 was used to equally divide the whole emission of bacteria/meat into two channels A1/A2. As measured by a Cary spectrophotometer the transmittance of the beam splitter at 45° gave a 5% fluctuation from 450 nm to 650 nm. The reflected beam, which is assigned as signal, is then filtered by a long pass filter 111 allowing wavelengths longer than 450 nm to be detected by the PMT 114. The transmitted beam A2, which is assigned as reference, is also filtered at 113 so that wavelengths longer than 580 nm are detected by the other PMT 115. Typical responsivity of visible PMTs dies off at ~800 nm. Thus the PMTs 114/115 are measuring integrated photoluminescence intensities over 800-450 nm and 800-580 nm, respectively for the signal and the reference.

A LabView program was used to acquire voltages from each PMT 114/115. An arbitrary output number is generated using the ratio of the signal and the reference voltages at a rate of 6.67 Hz. The positive result is defined when the output number exceeds 80.00 and a virtual red LED on a computer screen lights for attention otherwise a green LED lights.

2.2. Experiment

Lamb samples were provided both from a slaughter house and a local butchery in Canterbury, New Zealand. All the samples were then stored in a household refrigerator prior to testing. The temperature inside the refrigerator was monitored over 24 hr and measured to be −0.62° C. in average. No inoculums were performed as the target bacteria was expected to propagate with time. Prior to testing, the samples were excised into 5.0 $cm^2$ size and were put into Petri dishes. The samples were then left in an air conditioned lab for up to three days. The monitored temperature in the lab was 21.1±0.3° C. The sample preparation was done sequentially to allow a good distribution of bacteria growth with time.

To validate the bacteria detector a CCD equipped spectrometer 300 was used simultaneously for comparison. As shown in FIG. 1, an additional fibre 310 is placed at ~45 degrees normal to the sampling surface 210. The signal collected from this fibre 310 is transmitted to the spectrometer 300 with an f number of f/4.1 and then the resolved spectra were recorded by the CCD fitted at the end slit of the spectrometer. The two fibres 130/310 were coupled using magnetic posts so that the bacteria detector 110 and the CCD would observe the same emission from the same spot of excitation.

After observing emission spectra and detector-readings, standard bacterial enumerations were performed to the same samples. For the enumeration the samples were sent to Environmental Science and Research, Christchurch, New Zealand, within half an hour of measurements. Each sample was put into a broth solution and was mechanically shaken. The resultant solution is then spread onto nutrient agar plates optimized for *Pseudomonas*. After for 24 hours of incubation at 23° C., the bacteria were counted in terms of colony-forming unit (cfu)/$cm^2$.

2.3. Results and Analysis

In order to verify the spectral regions for detecting signal and reference, emission spectra of bacteria from a 13 day old sample were observed as shown in FIG. 2. After exposing the sample to room temperature and atmosphere for 53 hours, a drastic increase of PL intensity was observed (square), compared to the spectrum taken immediately after unpacking (circle). The spectra evidently show that increased PL intensity is directly related to the growth of bacteria on meat surfaces. The dynamic change among the PL spectra was non-uniform throughout the spectral range. The most sensitive region to detect bacteria emission was at ~497 nm which gave the most dynamic change in the PL intensity. On the other hand wavelengths beyond ~580 nm gave the minimum increase of PL intensity suggesting less number of bacteria is contributing in that emission range. These observations led to the selection of appropriate optics for bacteria and reference detections, respectively. Due to the weak PL intensities narrow band pass filters were not used. Instead long pass filters were used to enhance detection for signal and reference emission. For the signal detection a long pass filter with an onset of ~450 nm was used to ensure the laser excitation is eliminated. For the reference detection another long pass filter with an onset of ~580 nm was used. As a result each PMT was made detecting a wide range of emission wavelengths and the ratio of the signal and the reference is somewhat analogous equation (1) above.

The detector output defined in (1) should also be similar to the ratio of actual emission spectra of bacteria observed by the spectrometer. Integrated PL intensities of bacterial emission and reference are calculated using Igor Pro. As indicated in FIG. 2, the limits of the integrations were given by the optical filters used in the detection and the spectrometer limit.

Figure 3:
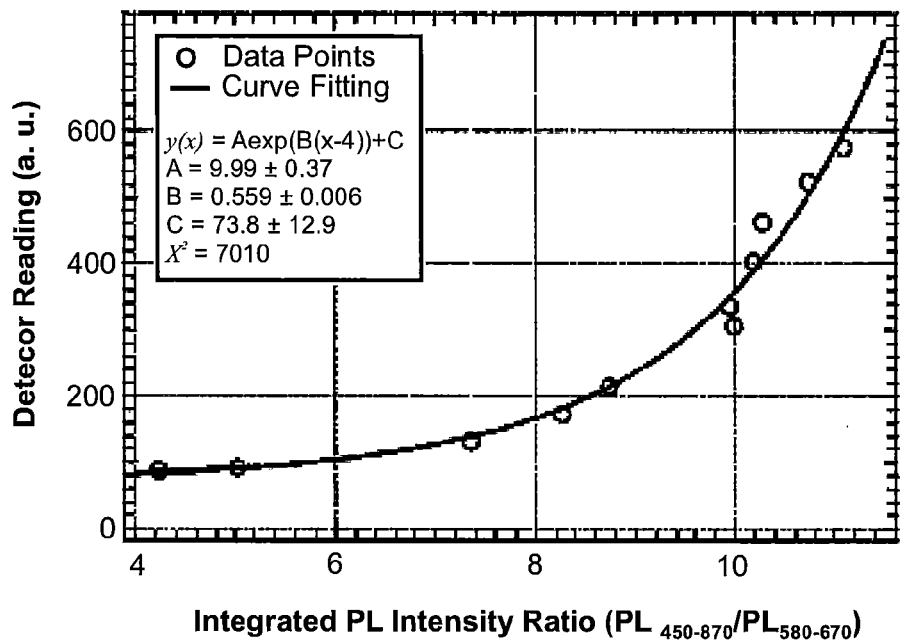
FIG. 3 is a graph showing the ratio of integrated light intensities and corresponding detector outputs of bacterial contamination on lamb samples.

To validate the detector performance with respect to spectroscopic measurements, the detector output and the ratio of bacteria emission and reference were compared as shown in FIG. 3. Each data point represents the ratio of integrated PL intensity measured by the CCD equipped spectrometer and the corresponding detector output at the same area of investigation under the same laser excitation. It was clearly seen that the detector output is proportional to the ratio of observed emission spectra of bacteria. An exponential curve fitting was performed using Igor Pro. The relationship between the detector output and the spectroscopic data is best described as the following equation:

$$y(x) = A\ \exp[B(x-4)] + C \qquad (2)$$

where
y=detector output
x=Integrated PL intensity ratio measured by CCD equipped spectrometer
A=Arbitrary fitting parameter, 9.99±0.37
B=Arbitrary fitting parameter, 0.559±0.006
C=Initial detector output for fresh meat, 73.8±12.9.

For fresh meat samples x is measured to be ~4 and hence used in (2). The value of $\chi^2$ was 7010 and σ was 25.2. The non linear relationship can be explained by the differences in operating mechanisms between CCDs and PMTs. CCDs accumulate charges generated by incoming photons while PMTs multiply charges. The dynamic range of the PMTs is then much higher than the CCDs.

Figure 4:
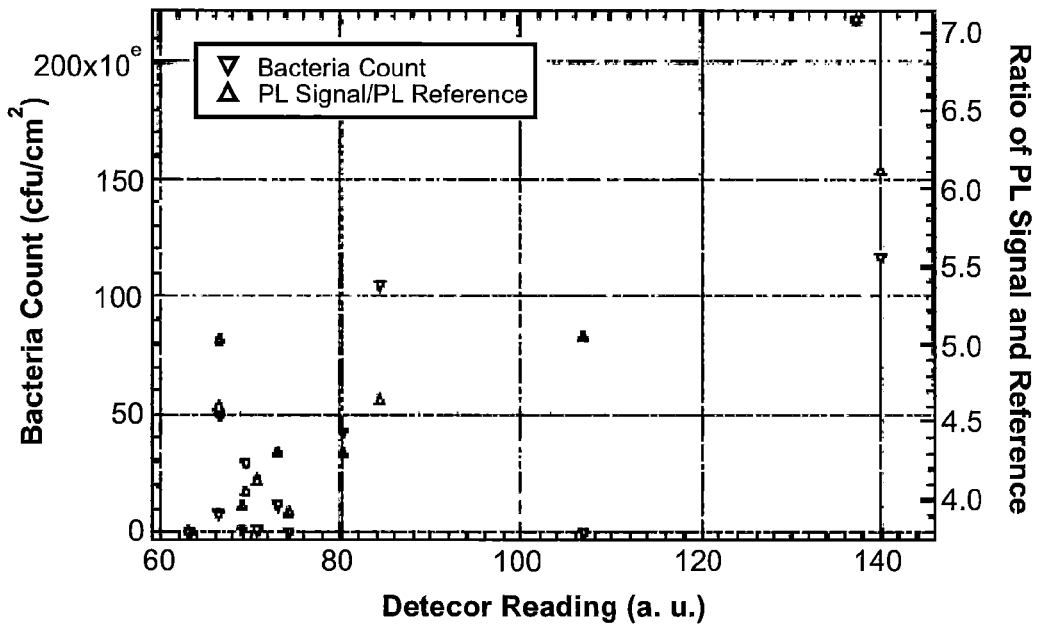
FIG. 4 is a chart showing enumeration (in units of cfu/cm$^2$) of *Pseudomonas* on surfaces of aged lamb samples with respect to the detector output (x-axis)

Additional experiments were carried out to scope the sensitivity of the detector 110 by comparing the detector readings with corresponding bacteria enumerations. It can be seen from FIG. 4 that the larger detector output gave, the higher the level of *Pseudomonas*. This is simply due to the fact that more contamination on the surface contributes to more emission intensity. Hence the PMTs 114/115 detected more photons. Without causing saturation in the PMTs 114/115 the detector 110 was able to detect bacteria levels between $10^2$ and $10^2$. However the actual bacteria concentration of 6500 cfu/cm$^2$ at ~$10^7$ detector output was found to be far less than that forecasted by the spectroscopic analysis which was ~$8 \times 10^7$ cfu/cm$^2$. A couple of possible explanations can be raised. Firstly some fragments of bone may also give efficient fluorescence emission. When the samples were purchased, a whole rib was cut into smaller pieces using an electric saw. Some bone fragments may have deposited on the surface of the samples and yielded a false result. Secondly other bacteria species may have contributed in the same detecting wavelength but not grown on the agar plates which have an optimum nutrient for *Pseudomonas*. Further identification study revealed that a couple of data points (indicated by circles in FIG. 4) have shown *Pseudomonas* as a minor species. *Staphylococcus* was the predominant for these data points. Following this the detector is not capable of differentiating between bacteria species when different species emit at the same detecting wavelength. Further development would involve pulsed excitation and the detection optimized to a specific time frame of *Pseudomonas* life time.

The device can detect *Pseudomonas* on surfaces of lamb meat down to the level of ~530 cfu/cm$^2$. The device 110 is real-time and gives an output in every 150 ms. Further improvements can be achieved by increasing tube voltages for the PMTs 114/115 which currently operate at the half of the maximum supply voltage. Also the output power of the 405 nm laser 120 can be increased as more powerful versions are available. In addition, differentiation in bacteria species is possible by adding a filter wheel to select different detecting region for other bacteria species. Finally, modulating current of the detector and the laser will provide further differentiation of bacteria as life times of excited state of molecules in bacteria are slightly different depending on the microbial environment.

Further improvement of the device 110 would include employing more sensitive PMTs 114/115 and having more fibre bundles 132/131 to increase transfer strength of bacteria fluorescence. In addition more powerful laser diode 120 is expected to give higher sensitivity.

The foregoing description of the invention includes preferred forms thereof. Modifications may be made thereto without departing from the scope of the invention as defined by the accompanying claims.

The invention claimed is:

1. Apparatus for detecting the presence of bacteria on a sample, the apparatus comprising:
    a light source arranged for illuminating a region of the sample with light having an excitation wavelength;
    a light transmission medium arranged for receiving and conducting light emitted by the region of the sample when illuminated by the light source;
    a detector connected to said light transmission medium comprising:
        a first longpass optical filter positioned for receiving the light from said light transmission medium, said first optical filter being adapted to transmit light within a first waveband that contains a light wavelength associated with a fluorescent property of a bacteria;
        a second longpass optical filter positioned for receiving the light from said light transmission medium, said second optical filter being adapted to transmit light within a second waveband that does not contain the light wavelength associated with the fluorescent property of the bacteria, but which otherwise overlaps with the first waveband;
        a first photomultiplier positioned to receive the light transmitted by said first optical filter and to generate a first signal that is indicative of the intensity of the light received from the first optical filter;
        a second photomultiplier positioned to receive the light transmitted by the second optical filter and to generate a second signal that is indicative of the intensity of the light received from the second optical filter;
    a memory component for storing data indicative of a predetermined threshold criteria associated with the bacteria;
    a processor connected to said first and second photomultipliers and to said memory component, said processor configured to:
        receive the first signal from the first photomultiplier;
        receive the second signal from the second photomultiplier;
        compare the first signal to the second signal by calculating a preselected mathematical relationship between a parameter of the first signal and a corresponding parameter of the second signal to provide a calculated criteria;
        compare the calculated criteria to the predetermined threshold criteria; and
        generate an output signal based on the comparison that is indicative of the presence or absence of bacteria on the sample; and
    an indicating device connected to receive the output signal and provide a perceptible indication of the presence or absence of bacteria on the sample.

2. The apparatus as claimed in claim 1 wherein the processor is configured to compare the first signal to the second signal by dividing a first value indicative of a strength of the first signal by a second value indicative of a strength of the second signal, and wherein the presence of the bacteria is identified by the processor when the output of the division is above a predetermined threshold value.

3. The apparatus as claimed in claim 1 wherein the first waveband has a shorter lower band limit wavelength than the second waveband.

4. The apparatus as claimed in claim 1 further comprising a beam splitter positioned between the light transmission medium and the first and second filters and arranged to receive a light beam emitted from the light transmission medium and split the beam into two beams traversing in different directions towards the first and second filters respectively.

5. The apparatus as claimed in claim 4 further comprising one or more excitation optical fibres coupled to the light source for receiving light from the light source and transmitting the light onto the sample, and the light transmission medium comprises one or more emission optical fibres for receiving emitted light from the sample and transmitting the emitted light to the beam splitter.

6. The apparatus as claimed in claim 5 wherein the one or more excitation optical fibres and the one or more emission optical fibres are optically coupled to a lens element adjacent the sample, the lens being arranged to yield an excitation light beam from the excitation optical fibre or fibres onto the region of the sample in one direction and yield an emission light beam emitted from the sample into the emission optical fibre or fibres in an opposite direction.

7. The apparatus as claimed in claim 2 wherein the processor is configured to determine the first and second values by integrating the first and second signals over the first and second wavebands respectively.

8. The apparatus as claimed in claim 1 wherein the excitation wavelength is shorter than or equal to the lower band limit wavelength of the first waveband.

9. The apparatus as claimed in claim 1 wherein the first waveband contains one or more wavelengths associated with the fluorescent properties of the bacteria *pseudomonas*.

10. The apparatus as claimed in claim 1 wherein the excitation wavelength is approximately 405 nm.

11. The apparatus as claimed in claim 1 wherein a lower cut-off limit of the first waveband is approximately 450 nm and a lower cut-off limit of the second waveband is approximately 580 nm.

12. The apparatus as claimed in claim 1 wherein the first waveband contains one or more wavelengths associated with the fluorescent properties of a substance associated with the bacteria.

13. The apparatus as claimed in claim 1 wherein the excitation wavelength is between approximately 350 nm and 650 nm.

14. The apparatus as claimed in claim 13 wherein the excitation wavelength is approximately 450 nm.

15. The apparatus as claimed in claim 13 wherein a lower cut-off limit of the first waveband is approximately 650 nm and a lower cut-off limit of the second waveband is approximately 720 nm.

16. The apparatus as claimed in claim 12 wherein the substance is chlorophyll, a metabolite of chlorophyll, or both.

* * * * *